(12) United States Patent
Bristow (10) Patent No.: US 10,015,967 B2
(45) Date of Patent: Jul. 10, 2018

(54) FORM OF ISOXADIFEN-ETHYL, A PROCESS FOR ITS PREPARATION AND USE OF THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: Rotam Agrochem International Company Limited, Chai Wan (HK)

( * ) Notice: Subject to any disclaimer, the term of this patent is extended or adjusted under 35 U.S.C. 154(b) by 7 days.

(21) Appl. No.: 14/926,377

(22) Filed: Oct. 29, 2015

(65) Prior Publication Data

US 2017/0118988 A1    May 4, 2017

(51) Int. Cl.
| | | |
|---|---|---|
| *A01N 47/36* | (2006.01) | |
| *C07D 261/04* | (2006.01) | |
| *A01N 43/80* | (2006.01) | |

(52) U.S. Cl.
CPC ........... *A01N 47/36* (2013.01); *C07D 261/04* (2013.01)

(58) Field of Classification Search
CPC ....... A01N 47/36; A01N 43/80; C07D 261/04
USPC ....................................................... 504/105
See application file for complete search history.

(56) References Cited

U.S. PATENT DOCUMENTS

| 3,836,351 | A | * | 9/1974 | Cooke | ............... | 504/168 |
| 5,516,750 | A | | 5/1996 | Willms et al. | | |
| 8,735,321 | B2 | * | 5/2014 | Troppmann | ........... | A01N 25/12 |
| | | | | | | 504/100 |
| 2008/0318786 | A1 | * | 12/2008 | Rosinger | ................ | A01N 41/10 |
| | | | | | | 504/139 |
| 2015/0031877 | A1 | * | 1/2015 | Hiratsuka | .............. | A01N 43/84 |
| | | | | | | 544/105 |

FOREIGN PATENT DOCUMENTS

CN    103172582 A    *  6/2013

OTHER PUBLICATIONS

McClurg, R.B., "X-ray Powder Diffraction(XRPD) to Describe Crystal Forms," Publication of SSCI an Aptiuit Company, Jul. 9, 2008, pp. 1-23.*
McClurg ,"X-Ray Powder Diffraction (XRPD) to Describe Crystal Forms," Publication of SSCI an Aptuit Company, U Jul. 9, 2008, pp. 1-23.*
McClurg ,"X-Ray Powder Diffraction (XRPD) to Describe Crystal Forms," Publication of SSCI an Aptuit Company, Jul. 9, 2008, pp. 1-23.*

* cited by examiner

*Primary Examiner* — Johann R Richter
*Assistant Examiner* — Courtney A Brown
(74) *Attorney, Agent, or Firm* — Dickinson Wright PLLC (57) ABSTRACT

A crystalline form of isoxadifen-ethyl of formula (I), the crystal preparation process, the analyses of the crystal through various analytical methods and using the crystal to prepare stable agrochemical formulation. The invention also describes the use of various solvents towards the crystalline form preparation conditions.

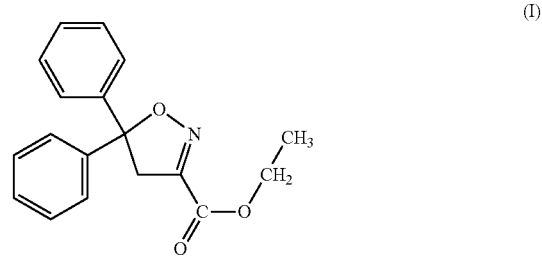

17 Claims, 4 Drawing Sheets

FORM OF ISOXADIFEN-ETHYL, A PROCESS FOR ITS PREPARATION AND USE OF THE SAME

BACKGROUND

Field

The present disclosure relates to a crystalline form of ethyl 4,5-dihydro-5,5-diphenyl-3-isoxazolecarboxylate (isoxadifen-ethyl), to its preparation processes and to its use in agrochemical preparations.

Description of Related Art

Ethyl 4,5-dihydro-5,5-diphenyl-3-isoxazolecarboxylate (isoxadifen-ethyl) is a potent safener for sulfonylurea herbicides. Isoxadifen-ethyl has molecular formula of $C_{18}H_{17}NO_3$. Its chemical structure is:

(I)

It is typically used to reduce the phototoxicity of sulfonylurea herbicides when applied on crops, such as maize, wheat and cereals.

The commercially available isoxadifen-ethyl, which is usually manufactured by the process described in U.S. Pat. No. 5,516,750, which is incorporated herein by reference for all purposes, is present in an amorphous state, the melting point which is about 78° C.-81° C.

SUMMARY

It has been found that isoxadifen-ethyl in amorphous state is highly unstable. It will generally undergo significant hydrolysis when dissolved or dispersed in water. Furthermore, hydrolysis can occur during storage, particularly where the compound is exposed to moisture. As a result, the stability of isoxadifen-ethyl is of great concern with respect to providing the commercially available formulations. Therefore, there is a need to provide a novel form of isoxadifen-ethyl with increased stability in formulations.

Accordingly, in an embodiment, the invention provides a novel crystalline form of isoxadifen-ethyl, termed "crystalline modification I", and a process for its preparation, as well as agrochemical compositions containing it, and methods for using it in agrochemical applications, such as methods for applying it to plants, plant loci, and plant parts. The novel crystalline modification I has been found to have increased stability relative to the amorphous form. Accordingly, in an embodiment, the invention also provides compositions for controlling undesirable plant growth, such as weeds, comprising the crystalline modification I of isoxadifen-ethyl with sulfonylurea herbicides, as a mixture with auxiliaries and carriers. The use of the crystalline modification I of isoxadifen-ethyl with sulfonylurea herbicides in the control of undesired plant growth and a method for the same are also provided by embodiments of the invention.

BRIEF DESCRIPTION OF DRAWINGS

Various features and aspects of the embodiments of the invention disclosed herein can be more clearly understood by reference to the drawings, which are intended to exemplify and illustrate, but not to limit, the scope of the invention, and wherein.

DETAILED DESCRIPTION OF SPECIFIC EMBODIMENTS

The invention can be more clearly understood by reference to the following detailed description of specific embodiments thereof, which is intended to illustrate, but not limit, the scope of the appended claims.

It has been found that an embodiment of the crystalline modification I of isoxadifen-ethyl has a significant increase in its stability when mixing with sulfonylurea herbicides in formulations that are otherwise similar to current commercially available formulations, which contain the amorphous form of isoxadifen-ethyl. In addition, it has been found that the crystalline modification I of isoxadifen-ethyl is easier to comminute or grain compared to amorphous isoxadifen-ethyl prepared in accordance with the disclosure of U.S. Pat. No. 5,516,750. This allows the preparation of commercial formulations such as suspension concentrates (SC), oil-based suspension concentrates (OD), water-dispersible granules (WG) and water-soluble granules (SG). Hence, it is possible to prepare any formulations of isoxadifen-ethyl in crystalline modification I when mixing with sulfonylurea herbicides, as will be disclosed hereinafter.

By virtue of its high stability, the crystalline modification I of isoxadifen-ethyl when mixing with sulfonylurea herbicides is highly suitable for preparing compositions for controlling undesirable weeds.

According to a first aspect of the invention, a crystalline modification I of isoxadifen-ethyl is provided, exhibiting at least 3 of the following reflexes as 2θ values, in any combination thereof, in an X-ray powder diffractogram recorded using Cu—Kα radiation at 25° C.:

| | |
|---|---|
| 2θ=11.027±0.2 | (1) |
| 2θ=17.841±0.2 | (2) |
| 2θ=19.492±0.2 | (3) |
| 2θ=19.841±0.2 | (4) |
| 2θ=20.583±0.2 | (5) |
| 2θ=22.151±0.2 | (6) |
| 2θ=22.920±0.2 | (7) |
| 2θ=23.541±0.2 | (8) |
| 2θ=24.801±0.2 | (9) |
| 2θ=25.775±0.2 | (10) |

2θ=26.895±0.2 (11)

2θ=27.813±0.2 (12)

2θ=29.408±0.2 (13)

2θ=30.065±0.2 (14)

2θ=31.228±0.2 (15)

2θ=33.502±0.2 (16)

Figure 2:
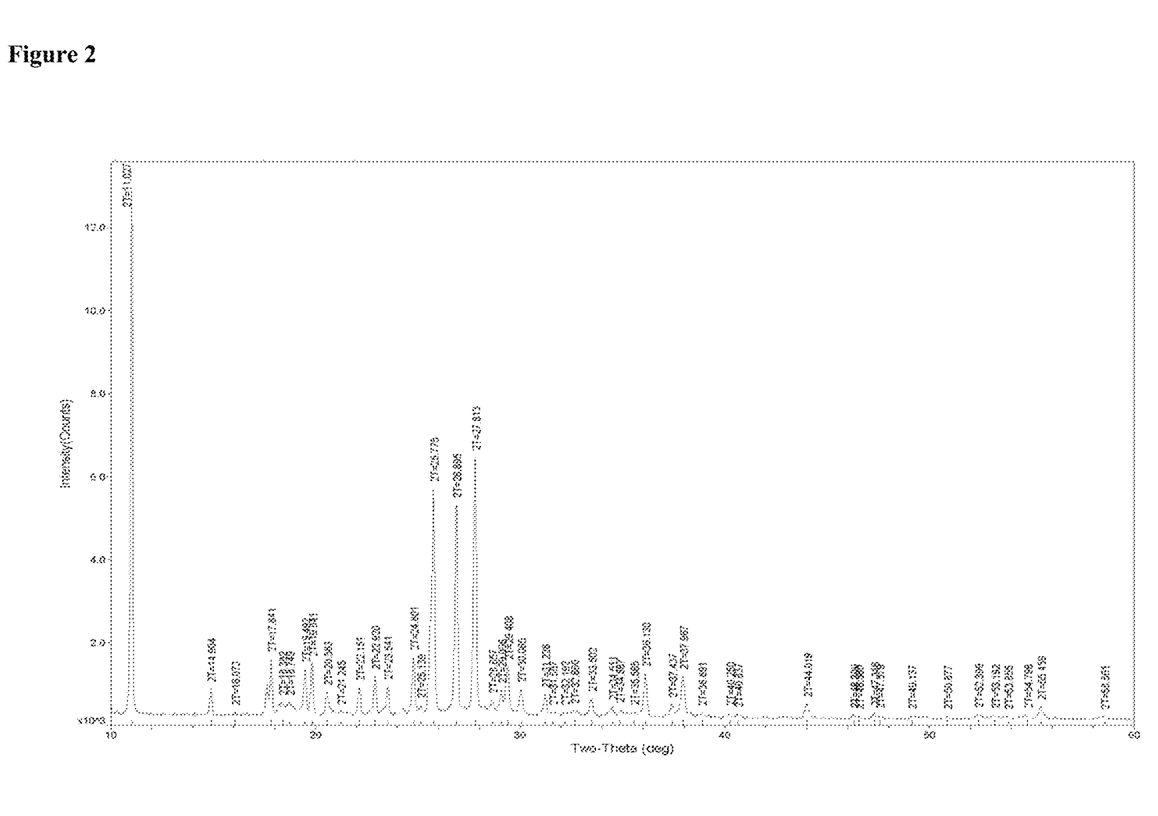
FIG. 2 is a powder X-ray diffractogram of an embodiment of crystalline modification I of isoxadifen-ethyl.

The crystalline modification I of isoxadifen-ethyl of an embodiment of the invention is characterized by an X-ray powder diffractogram having at least three of the reflexes indicated above, in any combination. This means that the crystalline modification I of an embodiment of isoxadifen-ethyl can contain 3 or more of the reflexes indicated above in any combination of reflexes. For example, the crystalline modification I of an embodiment of isoxadifen-ethyl can contain at least reflexes (1), (2), and (3), or at least reflexes (2), (3), and (4), or reflexes (1), (3), and (4), or any other combination of at least three reflexes. Preferably, the crystalline modification I is one having at least four of the aforementioned reflexes, more preferably at least five, six or seven, or eight of said reflexes, again in any combination. An X-ray powder diffractogram of the crystalline modification I of isoxadifen-ethyl is shown in FIG. 2, which will be described in detail hereinafter.

According to a preferred embodiment the crystalline form A exhibits at least 3, 4, or 5 or all of the reflexes, in any combination, from the following:

2θ=11.027±0.2 (1)

2θ=17.841±0.2 (2)

2θ=19.492±0.2 (3)

2θ=19.841±0.2 (4)

2θ=24.801±0.2 (9)

2θ=25.775±0.2 (10)

2θ=26.895±0.2 (11)

2θ=27.813±0.2 (12)

The crystalline modification I of isoxadifen-ethyl according to an embodiment of the invention may be further characterized by Infrared (IR) spectroscopy. The IR spectrum of the crystalline modification I is showed in FIG. 1 with characteristic bands at one or more of 2984.31, 2928.19, 2160.89, 1978.81 and 1716.65 $cm^{-1}$.

All IR spectra were obtained using the following acquisition parameters:

| | |
|---|---|
| FT-IR spectrometer | Bruker Tensor37 |
| Diamond ATR unit | from Specac |
| Wavelength range | 550-4000 $cm^{-1}$ |
| Resolution | 4 $cm^{-1}$ |
| Number of scans | 16 |

Figure 3:
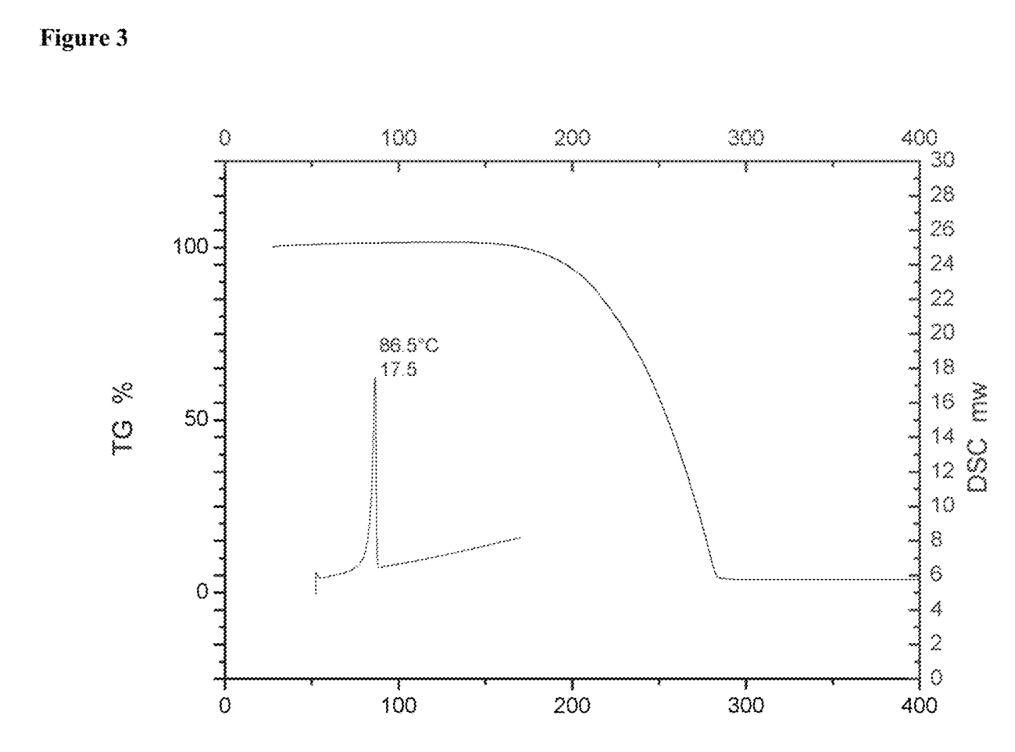
FIG. 3 is a graph showing the results of a Differential Scanning Calorimetry (DSC) scan of an embodiment of crystalline modification I of isoxadifen-ethyl.

The crystalline modification I of isoxadifen-ethyl according to an embodiment of the invention may be further characterized by differential scanning calorimetry (DSC) (FIG. 3). The DSC spectrum of the crystalline modification I of isoxadifen-ethyl exhibits an endothermic peak at 86.5° C. as shown in FIG. 3.

Methods for preparing amorphous isoxadifen-ethyl are known in the art. Amorphous isoxadifen-ethyl is manufactured and available on a commercial scale. A particularly suitable method for preparing amorphous isoxadifen-ethyl is described in U.S. Pat. No. 5,516,750.

According to an embodiment of the invention, the crystalline modification I of isoxadifen-ethyl can be obtained by the processes below:

Isoxadifen-ethyl in amorphous state is dissolved and then crystallized from solvents.

In one aspect, the present invention provides a process for preparing a crystalline modification I of isoxadifen-ethyl comprising steps of:

i) preparing a solution of an amorphous isoxadifen-ethyl in a solvent;

ii) effecting crystallization of isoxadifen-ethyl from the solution to obtain a solid precipitate; and iii) isolating the solid precipitate.

Suitable solvents for preparing isoxadifen-ethyl crystalline modification I include acetonitrile, halogenated hydrocarbons (for example, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane), cymene, petroleum fractionshaving a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol), and mixtures of any of these.

Preferred solvents include acetonitrile, ethers, aromatic hydrocarbons (such as benzene, toluene, xylene, chlorobenzene), esters and aliphatic alcohols and mixtures thereof. Particularly preferred solvents or solvent mixtures include isopropanol, toluene, methyl-tetrahydrofuran, diethyl carbonate, chlorobenzene, n-butyl acetate, isobutyl acetate, n-butanol, methanol, ethanol, ethyl malonate, methyl t-butyl ether, and mixtures of these, particularly mixtures of toluene and butanol, mixtures of toluene and n-butyl acetate, mixtures of ethyl malonate and methyl t-butyl ether, as well as mixtures of butyl acetate and methyl t-butyl ether. Solvent mixtures of more than 2 or 3 or 4 components are also envisaged by embodiments of the invention.

In the invention, it is preferred that the solvent comprises an alcohol and/or acetonitrile, including mixtures thereof, with other solvents or particularly with each other.

Hence, according to a preferred embodiment in step (i), amorphous isoxadifen-ethyl is dissolved in a solvent comprising methanol, or acetonitrile, or a mixture thereof.

In step (ii), isoxadifen-ethyl is crystallized from the solution. Techniques for effecting crystallization of isoxadifen-ethyl from the solution are known to those skilled in the art. For example, in an embodiment where the solution in step (i) is formed at elevated temperatures, crystallization may be effected by cooling the solution to room or ambient temperature. In one preferred embodiment, crystallization is effected by concentrating the solution formed in step (i) of the process by removal of solvent. Alternatively, or in addition thereto, seed crystals, in particular seed crystals of the aforementioned crystalline modification I of isoxadifen-ethyl, may be added to the solution formed in step (i), to facilitate and/or enhance crystallization.

It is preferred that the solid precipitate of isoxadifen-ethyl recovered during the crystallization stage is washed with a solvent for one or more times. Preferably, the solvent employed in the washing stage consists of one or more components of the solvent employed for forming the solution in step (i), as described hereinbefore. Methanol and acetonitrile, and mixtures thereof are particularly suitable solvents for washing the recovered solid of isoxadifen-ethyl.

The invention, in an embodiment, also relates to a composition comprising the crystalline modification I of isoxadifen-ethyl and a herbicidally effective amount of sulfonylurea herbicides. The weight ratio of the isoxadifen-ethyl to sulfonylurea herbicides varies within wide limits and is preferably in a range of about 1:10 to about 10:1, in particular in a range of about 1:10 to about 5:1.

The amount of sulfonylurea herbicides in the formulation can be less than about 70% by weight of the formulation, preferably less than about 50% by weight of the formulation, particularly preferably about 25% by weight of the formulation.

The use of amorphous isoxadifen-ethyl as a safener for sulfonylurea herbicides is known in the art and is used on a commercial scale. The crystalline modification I of isoxadifen-ethyl is also active in reducing the phototoxicity of sulfonylurea herbicides when controlling weeds. Techniques of formulating and applying amorphous isoxadifen-ethyl and sulfonylurea herbicides are known in the art. Isoxadifen-ethyl in the crystalline modification I of the present invention may be formulated and applied in an analogous manner with sulfonylurea herbicides.

Accordingly, in a further aspect, the invention provides a herbicidal composition comprising isoxadifen-ethyl in the crystalline modification I, as defined hereinbefore, with sulfonylurea herbicides.

Accordingly, an embodiment of the invention furthermore provides processes for preparing compositions for controlling weeds using the crystalline modification I of isoxadifen-ethyl together with sulfonylurea herbicides.

The crystalline modification I of isoxadifen-ethyl together with sulfonylurea herbicides can be incorporated in a known manner to the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using herbicidally acceptable auxiliaries, carriers and solvents.

These formulations are prepared by mixing the crystalline modification I of isoxadifen-ethyl and sulfonylurea herbicides in amounts of each analogous to those used for amorphous isoxadifen-ethyl with customary additives, for example, liquid diluents, solid diluents, wetting agents, dispersants, thickening agents, antifoaming agent and other formulation ingredients.

Sulfonylurea herbicides suitable for safening by the crystalline modification I of isoxadifen-ethyl include, but are not limited to, amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron and salts thereof, and mixtures thereof.

The following sulfonylureas are preferred for safening by the crystalline modification I of isoxadifen-ethyl in accordance with an embodiment of the invention: bensulfuron-methyl, flupyrsulfuron-methyl, metsulfuron-methyl, nicosulfuron, rimsulfuron, sulfometuron-methyl, thifensulfuron-methyl, tribenuron-methyl, halosulfuron-methyl, iodosulfuron-methyl, mesosulfuron-methyl and salts thereof, and mixtures thereof.

Liquid diluents include, but are not limited to, water, N,N-dimethylmamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol, and mixtures of these.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol, and mixtures thereof. Examples of water-insoluble solid diluents include, but are not limited to clays, synthetic and diatomaceous silicas, calcium and magnesium silicates, titanium dioxide, aluminum, calcium and zinc oxide, and mixtures of these.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates, and mixtures of these. Alkyl naphthalene sulphonates, sodium salts are particularly useful for the composition of the invention Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates, and mixtures of these. Ligninsulfonates such as sodium ligninsulfonates are particularly useful for the composition of the invention. Naphthalene sulfonate-formaldehyde condensates, such as naphthalenesulfonic acid, polymers with formaldehyde, and sodium salts are particularly useful for the composition of an embodiment of the invention Thickening agents include, but are not limited to, guar gum, pectin, casein, carrageenan, xanthan gum, alginates, methylcellulose, hydroxyethylcellulose, hydroxypropylcellulose, and carboxymethylcellulose, and mixtures of these. Synthetic thickening agents include derivatives of the former categories, and also polyvinyl alcohols, polyacrylamides, polyvinylpyrrolidones, various polyethers, their copolymers as well as polyacrylic acids and their salts, and mixtures of these. Alkylpolyvinylpyrrolidones are particularly useful for the composition of the present invention Other formulation ingredients can also be used in the present invention such as dyes, defoamers, drying agents, and the like. These ingredients are known to one skilled in the art.

The crystalline modification I of isoxadifen-ethyl according to an embodiment of the invention can be present in formulations and in its use forms, prepared from these formulations, and as a safener to reduce the phototoxicity of sulfonylurea herbicides.

All plants, plant parts, and plant loci can be treated in accordance with the invention. In the present context, plants are to be understood as meaning all plants and plant populations such as desired and undesired wild plants or crop plants (including naturally occurring crop plants). Crop plants can be plants which can be obtained by conventional breeding and optimization methods, or by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included. Loci of plants include the environment near the plant and/or plant propagation materials, such as the soil in which the plant grows or will be sown, or the plant's surroundings.

As used herein, the term "about," when used in connection with a numerical amount or range, means somewhat more or somewhat less than the stated numerical amount or range, to a deviation of ±10% of the stated numerical amount or endpoint of the range.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like. Treatment of the plants and plant parts with the compositions or formulations of the inventions according to the invention is carried out directly or by allowing the compositions or formulations to act on their loci, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of the invention are seen most when the herbicidal composition is applied to kill weeds in growing crops of useful plants, such as maize (corn) including field corns, pop corns and sweet corns, cotton, wheat, barley, rye, triticale, rice, oats, potatoes, sugar beets, plantation crops (such as bananas, fruit trees, rubber trees, tree nurseries), vines, asparagus, bushberries (such as blueberries), caneberries, cranberries, flax, grain sorghum, okra, peppermint, rhubarb, spearmint and sugarcane. In this invention, treatment of growing crops of maize and potatoes are particularly beneficial.

All percentages are given in weight % unless otherwise indicated. Embodiments of the invention will now be described by way of the following examples which are provided for illustrative purposes only, and not intended to limit the scope of the disclosure or of the appended claims.

EXAMPLES

Example 1

Preparation of Amorphous Isoxadifen-ethyl in Accordance with the Disclosure of U.S. Pat. No. 5,516,750

13.52 g (0.075 mol) of 1,1-diphenylethene and 5.06 g (0.05 mol) of triethylamine are dissolved in 200 ml of ether at 0° C., and 7.58 g (0.05 mol) of ethyl 2-chloro-2-hydroximinoacetate, dissolved in 100 ml of ether, are subsequently added dropwise in the course of approximately two hours. After stirring has been continued for one hour at room temperature, 100 ml of $H_2O$ are added, and the mixture is subsequently extracted using ether. After drying over a $MgSO_4$, the ether is distilled off and the residue is purified over a silica gel column (eluent: n-heptane:ethyl acetate=8: 2). In this way, 12.7 g of product of melting point 78° C. to 81° C. are obtained.

Figure 4:
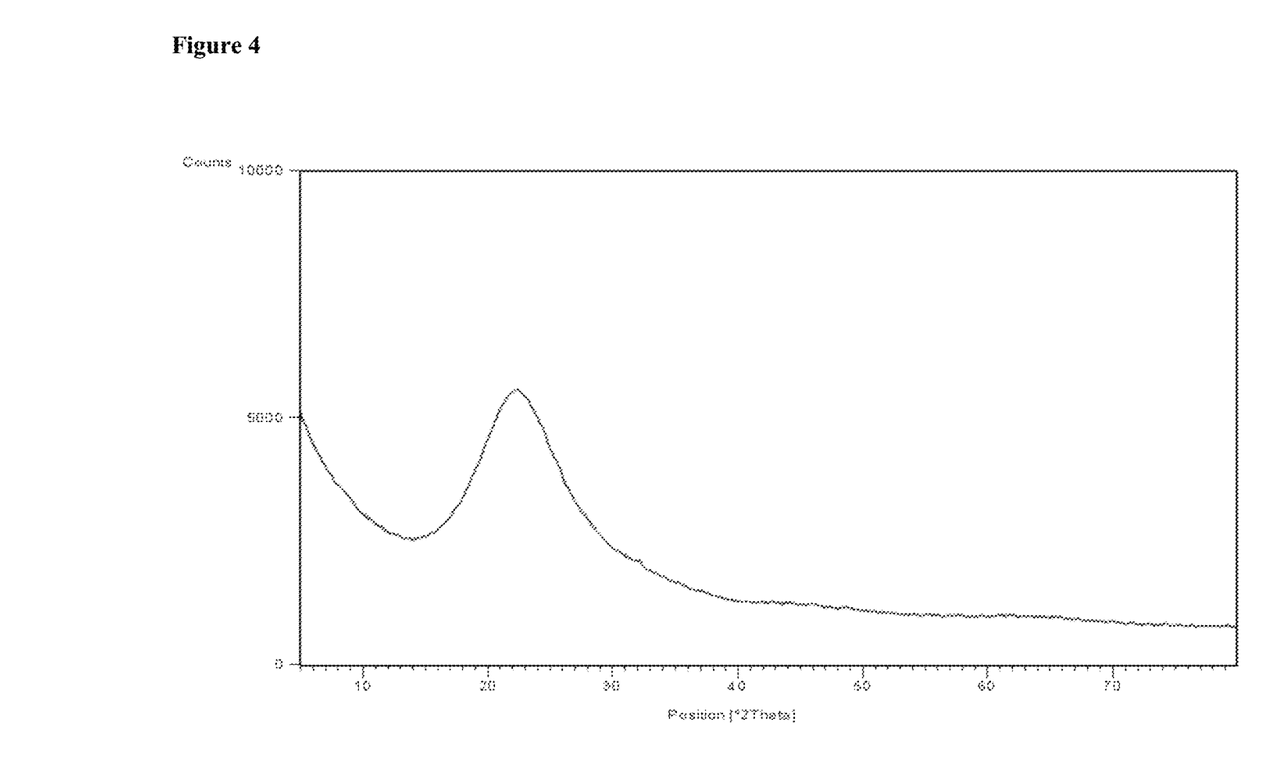
FIG. 4 is a graph showing the results of a powder X-ray diffractogram of amorphous isoxadifen-ethyl.

As shown in FIG. 4, the X-ray powder diffraction pattern of the resulting isoxadifen-ethyl products prepared above has no significant signals, which indicates the isoxadifen-ethyl product prepared in accordance with the disclosure of U.S. Pat. No. 5,516,750 is amorphous.

Example 2

Preparation of the Crystalline Modification I of Isoxadifen-ethyl

Crystallization from Methanol 10 ml methanol was charged into the reactor to dissolve crude, amorphous isoxadifen-ethyl prepared in Example 1 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with methanol. The resulting solid was dried under high vacuum to give crystals of pure isoxadifen-ethyl technical (Purity: 98%).

The crystals were characterized as being of the crystalline modification I of isoxadifen-ethyl using both IR spectrometry, X-ray powder diffraction and DSC.

Figure 1:
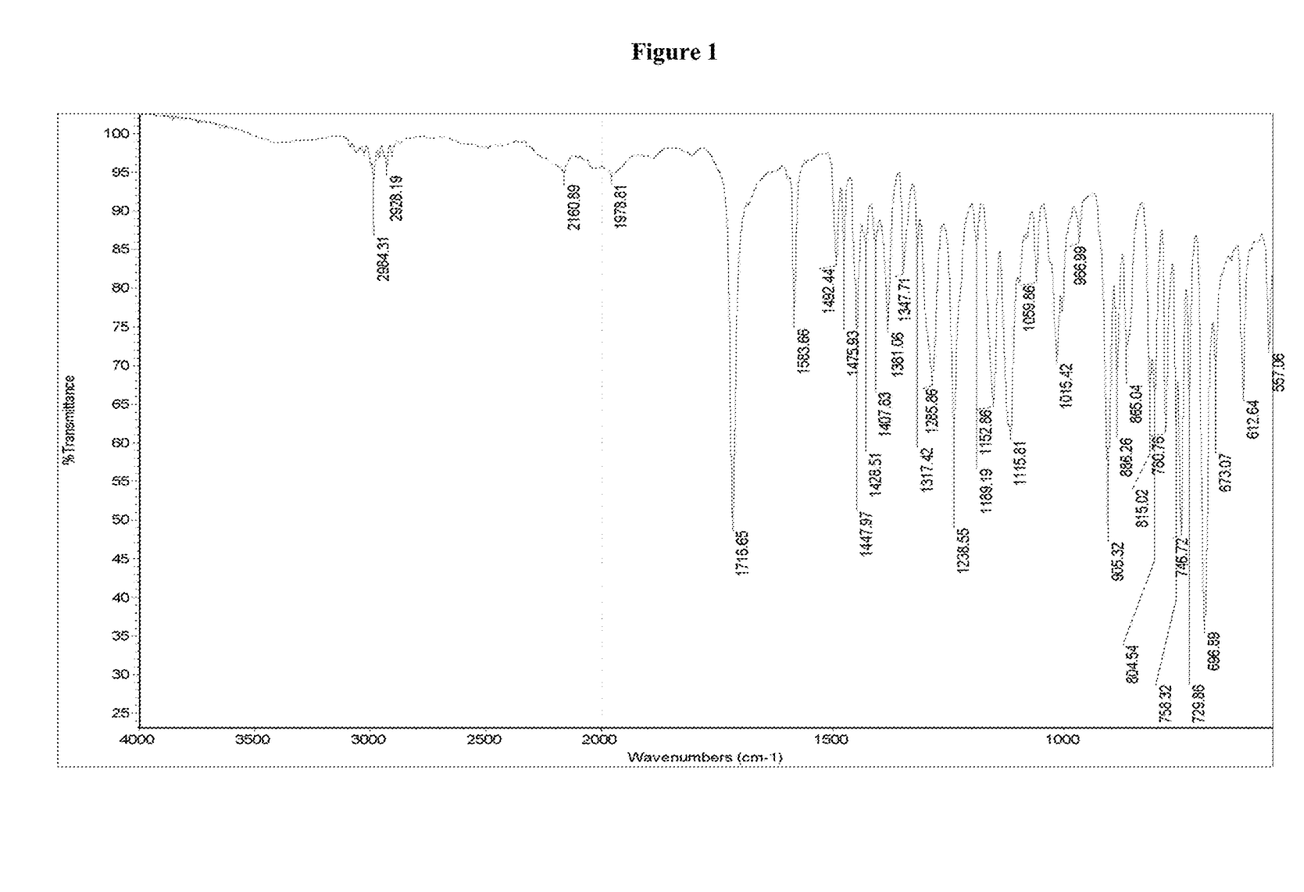
FIG. 1 is an infrared (IR) spectra of an embodiment of crystalline modification I of isoxadifen-ethyl.

The IR spectrum of the crystalline modification I of isoxadifen-ethyl is set out in FIG. 1. The IR spectrum exhibits characteristic peaks at 2984.31, 2928.19, 2160.89, 1978.81 and 1716.65 $cm^{-1}$.

The melting point of the product was measured by DSC and exhibits a peak at 86.5° C. as shown in FIG. 3.

The crystalline modification I of isoxadifen-ethyl has the X-ray powder diffractogram shown in FIG. 2 with the reflexes listed in Table 1 below.

TABLE 1

| Crystalline modification I | |
|---|---|
| 2θ (°) | d (Å) |
| 11.027 ± 0.2 | 9.31 ± 0.05 |
| 17.841 ± 0.2 | 5.77 ± 0.05 |
| 19.492 ± 0.2 | 5.28 ± 0.05 |
| 19.841 ± 0.2 | 5.19 ± 0.05 |
| 24.801 ± 0.2 | 4.17 ± 0.05 |
| 25.775 ± 0.2 | 4.01 ± 0.05 |
| 26.895 ± 0.2 | 3.85 ± 0.05 |
| 27.813 ± 0.2 | 3.72 ± 0.05 |

Example 3

Preparation of the Crystalline Modification I of Isoxadifen-ethyl

Crystallization from Acetonitrile 10 ml acetonitrile was charged into the reactor to dissolve crude, amorphous isoxadifen-ethyl prepared in Example 1 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with some acetonitrile. The resulting solid was dried under high vacuum to give crystals of pure isoxadifen-ethyl technical (Purity: 98%).

The crystals were characterized as being the crystalline modification I of isoxadifen-ethyl using IR spectrometry, X-ray powder diffraction and DSC as described in Example 2.

Example 4

Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate.

TABLE 2

| Ingredients | Weights % | | Function |
|---|---|---|---|
| Isoxadifen-ethyl, crystalline modification I, 98% (prepared in Example 2) | 10.20 | 0.00 | Safener |
| Amorphous isoxadifen-ethyl (prepared in Example 1) | 0.00 | 10.20 | Safener |
| Tribenuron-methyl, 98% | 40.80 | 40.80 | Active compound |
| Sodium lignosulfonate (REAX ® 88B) | 12.00 | 12.00 | Dispersing agent |
| Alkylpolyvinylpyrrolidone | 10.00 | 10.00 | Thickening agent |
| Corn oil | Balance to 100% | Balance to 100% | Carrier |

Example 5

Preparation of Soluble Granules (SG)

All the components listed in Table 3 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 3

| Ingredients | Weights % | | Function |
|---|---|---|---|
| Isoxadifen-ethyl, crystalline modification I, 98% (prepared in Example 2) | 7.14 | 0.00 | Safener |
| Amorphous isoxadifen-ethyl (prepared in Example 1) | 0.00 | 7.14 | Safener |
| Metsulfuron-methyl, 98% | 25.51 | 25.51 | Active compound |
| Lignosulfonic acid, sodium salt, (REAX ® 88B) | 15.00 | 15.00 | Dispersing agent |
| Naphthalenesulfonic acid, polymer with formaldehyde, sodium salt (TAMOL ® NN 8906) | 6.00 | 6.00 | Dispersing agent |
| Sodium acetate | 4.00 | 4.00 | Filler |
| Sodium carbonate | 4.00 | 4.00 | Filler |
| Non-ionic aqueous emulsion of Polydimethylsiloxanes | 1.00 | 1.00 | Antifoaming agent |
| Mannitol | Balance to 100% | Balance to 100% | carrier |

Example 6

Preparation of Water Dispersible Granules (WG)

All the components listed in Table 4 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
|---|---|---|---|
| Isoxadifen-ethyl, crystalline modification I, 98% (prepared in Example 2) | 7.14 | 0.00 | Safener |
| Amorphous isoxadifen-ethyl (prepared in Example 1) | 0.00 | 7.14 | Safener |
| Metsulfuron-methyl, 98% | 25.51 | 25.51 | Active compound |
| Alkyl naphthalene sulphonate, sodium salt (Akzo Nobel) | 2 | 2 | Wetting agent |
| Lignosulfonic acid, sodium salt, REAX ® 88B) | 15 | 15 | Dispersing agent |
| Naphthalenesulfonic acid, polymer with formaldehyde, sodium salt (TAMOL ® NN8906) | 6 | 6 | Dispersing agent |
| Sucrose | 10 | 10 | Filler |
| Non-ionic aqueous emulsion of Polydimethylsiloxanes | 1 | 1 | Antifoaming agent |
| Mannitol | Balance to 100% | Balance to 100% | Carrier |

Example 7

Stability Test

The stability of the isoxadifen-ethyl in these compositions was determined by aging samples in heated ovens having the same atmosphere therein, and then comparing the isoxadifen-ethyl content before and after aging to determine relative percentage of hydrolysis (RPH). RPH was calculated by the following equation:

$$RPH = \frac{\text{(The final weight \% of isoxadifen-ethyl-}}{\text{The initial weight \% of isoxadifen-ethyl}} \times 100\%$$

Isoxadifen-ethyl content was determined by assaying the compositions with high-pressure liquid chromatography (HPLC) using reverse phase columns and eluants.

Samples prepared in Examples 4, 5 and 6 were stored at 54° C. for 1 week. The procedures are followed according to CIPAC MT 46.3. The concentration of isoxadifen-ethyl was measured at the end of each storage time by HPLC. The results are listed in Table 5.

TABLE 5

| Sample | Compound | Weight (%) of Isoxadifen-ethyl | RPH % |
|---|---|---|---|
| Example 4 | Isoxadifen-ethyl, crystalline modification I | 10 | 0 |
|  | Amorphous isoxadifen-ethyl | 10 | 50 |
| Example 5 | Isoxadifen-ethyl, crystalline modification I | 7 | 0 |
|  | Amorphous isoxadifen-ethyl | 7 | 40 |
| Example 6 | Isoxadifen-ethyl, crystalline modification I | 7 | 0 |
|  | Amorphous isoxadifen-ethyl | 7 | 45 |

The invention claimed is:

1. A crystalline modification I of isoxadifen-ethyl, exhibiting each of the following reflexes, in any combination, in an X-ray powder diffractogram recorded using Cu—Kα radiation at 25° C.:

$2\theta = 11.027 \pm 0.2$ (1)

$2\theta = 17.841 \pm 0.2$ (2)

$2\theta = 19.492 \pm 0.2$ (3)

$2\theta = 19.841 \pm 0.2$ (4)

$2\theta = 20.583 \pm 0.2$ (5)

$2\theta = 22.151 \pm 0.2$ (6)

$2\theta = 22.920 \pm 0.2$ (7)

$2\theta = 23.541 \pm 0.2$ (8)

$2\theta = 24.801 \pm 0.2$ (9)

$2\theta = 25.775 \pm 0.2$ (10)

$2\theta = 26.895 \pm 0.2$ (11)

$2\theta = 27.813 \pm 0.2$ (12)

$2\theta = 29.408 \pm 0.2$ (13)

$2\theta = 30.065 \pm 0.2$ (14)

$2\theta = 31.228 \pm 0.2$ (15)

$2\theta = 33.502 \pm 0.2$ (16).

2. The crystalline modification I of isoxadifen-ethyl according to claim 1, exhibiting an IR spectrum with one or more of the characteristic bands at 2984.31, 2928.19, 2160.89, 1978.81 and 1716.65 cm$^{-1}$.

3. The crystalline modification I of isoxadifen-ethyl according to claim 1, exhibiting a DSC spectrum having an endothermic peak at 86.5° C.

4. A process for the preparation of a crystalline modification I of isoxadifen-ethyl according to claim 1, comprising:
　i) preparing a solution of an amorphous isoxadifen-ethyl in a solvent, wherein the solvent is methanol, acetonitrile, or a mixture thereof;
　ii) effecting crystallization of isoxadifen-ethyl from the solution to obtain a solid precipitate; and
　iii) isolating the solid precipitate.

5. The process according to claim 4, wherein the solvent comprises acetonitrile.

6. The process according to claim 5, wherein the solvent comprises methanol.

7. A composition comprising a safening amount of the crystalline modification I of isoxadifen-ethyl according to claim 1, a herbicidally effective amount of at least one sulfonylurea herbicide, and at least one herbicidally acceptable auxiliary.

8. The composition in claim 7, in the form of a suspension concentrate (SC), an oil-based suspension concentrate (OD), a water-soluble granule (SG), a dispersible concentrate (DC), an emulsifiable concentrate (EC), an emulsion seed dressing, a suspension seed dressing, a granule (GR), a microgranule (MG), a suspoemulsion (SE) or a water-dispersible granule (WG).

9. The composition according to claim 8, in the form of an oil-based suspension concentrate (OD).

10. The composition according to claim 8, in the form of a water-soluble granule (SG).

11. The composition according to claim 8, in the form of a water-dispersible granule (WG).

12. The composition according to claim 7, wherein the auxiliary is selected from one or more of a solvent, a diluent, a wetting agent, a dispersant, and a thickening agent and an antifoaming agent.

13. The composition according to claim 7, wherein the weight ratio of the isoxadifen-ethyl to sulfonylurea herbicides is in a range of about 1:10 to about 10:1.

14. A method of controlling unwanted plant growth, comprising applying to the plant an effective amount of a composition according to claim 7.

15. The composition according to claim 7, wherein the sulfonylurea herbicide comprises one or more selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron and salts thereof, and mixtures thereof.

16. The composition according to claim 15, wherein the sulfonylurea herbicide comprises one or more selected from the group consisting of bensulfuron-methyl, flupyrsulfuron-methyl, metsulfuron-methyl, nicosulfuron, rimsulfuron, sulfometuron-methyl, thifensulfuron-methyl, tribenuron-methyl, halosulfuron-methyl , iodosulfuron-methyl, mesosulfuron-methyl and salts thereof, and mixtures thereof.

17. The composition according to claim 13, wherein the weight ratio of the isoxadifen-ethyl to sulfonylurea herbicides is in particular in a range of about 1:10 to about 5:1.

\* \* \* \* \*